United States Patent
Pardo et al.

(10) Patent No.: US 8,064,994 B2
(45) Date of Patent: Nov. 22, 2011

(54) CERVICAL VAGAL STIMULATION INDUCED WEIGHT LOSS

(75) Inventors: Jose V. Pardo, Eagan, MN (US); Sohail A. Sheikh, Napier (NZ)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 1145 days.

(21) Appl. No.: 10/541,853

(22) PCT Filed: Jan. 14, 2004

(86) PCT No.: PCT/US2004/000889
§ 371 (c)(1),
(2), (4) Date: Jun. 2, 2006

(87) PCT Pub. No.: WO2004/064918
PCT Pub. Date: Aug. 5, 2004

(65) Prior Publication Data
US 2006/0259077 A1    Nov. 16, 2006

Related U.S. Application Data

(60) Provisional application No. 60/439,824, filed on Jan. 14, 2003.

(51) Int. Cl.
*A61N 1/18*    (2006.01)
(52) U.S. Cl. ............................................. 607/2; 607/118
(58) Field of Classification Search ................ 607/2, 45, 607/115, 116, 118
See application file for complete search history.

(56) References Cited

U.S. PATENT DOCUMENTS

| 4,573,481 A | 3/1986 | Bullara |
| 4,702,254 A | 10/1987 | Zabara |
| 4,979,511 A | 12/1990 | Terry, Jr. |
| 5,154,172 A | 10/1992 | Terry, Jr. et al. |
| 5,179,950 A | 1/1993 | Stanislaw |

(Continued)

FOREIGN PATENT DOCUMENTS

WO    WO 02/04068 A1    1/2002

(Continued)

OTHER PUBLICATIONS

PCT International Search Report and the Written Opinion in International App. No. PCT/US2004/000889 (14 pp.)

(Continued)

*Primary Examiner* — Carl H Layno
*Assistant Examiner* — Allen Porter, Jr.
(74) *Attorney, Agent, or Firm* — Dinesh Agarwal, P.C.

(57) ABSTRACT

Apparatus and methods for treating obesity using chronic cervical vagal nerve stimulation (cVNS) of the left vagus trunk are disclosed. Four men and ten women, average age 46 years (SD±10) were treated with output current typically 0.75 mA, pulse frequency 30 Hz and width 250 or 500 µs, and duty cycle of 30 s power per five minutes. Mean intake weight was 91 kg (SD±27, range 46 to 137 kg) with body mass index (BMI) 43 kg/m$^2$ (SD±5, range 18 to 49 kg/mn$^2$). After 6-12 months, obese patients had marked weight loss while normal weights were maintained. Decrease in BMI was consistently proportional to initial BMI. Average weight loss at one year was 7 kg (SD±3, range −6 to +24) with mean drop in BMI of 2 kg/m$^2$ (SD±3, range −2 to +8)k. All patients denied any major dieting or exercise.

9 Claims, 6 Drawing Sheets

U.S. PATENT DOCUMENTS

| | | | |
|---|---|---|---|
| 5,186,170 | A | 2/1993 | Varrichio et al. |
| 5,188,104 | A | 2/1993 | Wernicke et al. |
| 5,215,086 | A | 6/1993 | Terry, Jr. et al. |
| 5,222,494 | A | 6/1993 | Baker, Jr. |
| 5,231,988 | A | 8/1993 | Wernicke et al. |
| 5,235,980 | A | 8/1993 | Varrichio et al. |
| 5,263,480 | A | 11/1993 | Wernicke et al. |
| 5,269,303 | A | 12/1993 | Wernicke et al. |
| 5,292,344 | A | 3/1994 | Douglas |
| 5,299,569 | A | 4/1994 | Wernicke et al. |
| 5,304,206 | A | 4/1994 | Baker, Jr. et al. |
| 5,330,513 | A | 7/1994 | Nichols et al. |
| 5,330,515 | A | 7/1994 | Rutecki et al. |
| 5,335,657 | A | 8/1994 | Terry, Jr. et al. |
| 5,540,730 | A | 7/1996 | Terry, Jr. et al. |
| 5,571,150 | A | 11/1996 | Wernicke et al. |
| 5,707,400 | A | 1/1998 | Terry, Jr. et al. |
| 5,722,998 | A | 3/1998 | Prutchi et al. |
| 5,928,272 | A | 7/1999 | Adkins et al. |
| 6,205,359 | B1 | 3/2001 | Boveja |
| 6,208,902 | B1 | 3/2001 | Boveja |
| 6,356,788 | B2 | 3/2002 | Boveja |
| 6,449,512 | B1 | 9/2002 | Boveja |
| 6,473,644 | B1 | 10/2002 | Terry, Jr. et al. |
| 6,587,719 | B1 * | 7/2003 | Barrett et al. ............ 607/2 |
| 6,609,025 | B2 | 8/2003 | Barrett et al. |
| 6,611,715 | B1 | 8/2003 | Boveja |
| 6,622,041 | B2 | 9/2003 | Terry, Jr. et al. |
| 6,622,047 | B2 | 9/2003 | Barrett et al. |
| 6,879,859 | B1 * | 4/2005 | Boveja ............ 607/45 |
| 2002/0077675 | A1 * | 6/2002 | Greenstein ............ 607/72 |
| 2002/0087192 | A1 * | 7/2002 | Barrett et al. ............ 607/2 |
| 2002/0161414 | A1 * | 10/2002 | Flesler et al. ............ 607/40 |
| 2002/0183237 | A1 | 12/2002 | Puskas |
| 2003/0045914 | A1 * | 3/2003 | Cohen et al. ............ 607/62 |
| 2003/0212440 | A1 | 11/2003 | Boveja |

FOREIGN PATENT DOCUMENTS

| | | |
|---|---|---|
| WO | WO 02/062291 A2 | 8/2002 |

OTHER PUBLICATIONS

Burneo J.G., Faught E., Knowlton R., Morawetz R., and Kuzniecky R. Weight loss associated with vagus nerve stimulation, Neurology 59(3):463-464 (Aug. 2002).

Byrd, Robert C. VA#03-029: Treatment of severe obesity with continuous, cervical, vagas nerve stimulation, Minneapolis, Minnesota, USA, National Technology Transfer Center, entire publication, Mar. 18, 2003 (24 pages).

Greene A.E., Todorova M.T. and Seyfried T.N. Perspectives on the metabolic management of epilepsy through dietry reduction of glucose and elevation of ketone bodies. Journal of Neurochemistry, 2003, 86:529-537.

Henry, Thomas R. Therapeutic mechanisms of vagas nerve stimulation. Neurology 59(Suppl 4) Sep. 2002, S3-S14.

Pardo J.V, Sheikh S.A., Rittberg B.R. and Adson D.E. Treatment of severe obesity with vagas nerve stimulation: An observational study. Washington 103094v1 (7 pages).

Pardo J.V., Sheikh S.A., Hages M.C., Lee J.T., Rittberg B.R. and Adson D.E. A Promising Novel Treatment for Severe Obesity: Cervical Stimulation of the Vagus Nerve and Associated Neural Circuitry. JAMA Format v5 Oct. 16, 2003 (24 pages).

Roslin M. and Kurian M. The Use of Electrical Stimulation of the Vagus Nerve to Treat Morbid Obesity. Epilepsy & Behavior 2, S11-S16 (2001).

Rush J.A., George M.S., Sackeim H.A., Marangell L.B., Husain M.M., Giller C., Nahas Z., Haines S., Simpson Jr. R.K. and Goodman R. Vagus Nerve Stimulation (VNS) for Treatment-Resistant Depressions: A Multicenter Study.Biol Psychiatry Feb. 15, 2000; 47(4):276-286.

Sobocki J., Thor PJ, Uson J., Diaz-Guemes I, Lipinski M., Calles C., and Pascual S. Microchip Vagal Pacing Reduces Food Intake and Body Mass. Hepato-Gastroenterology 2001; 48:1783-1787.

Pardo JV, Sheikh SA, Kuskowski MA, Surerus-Johnson C, Hages MC, Lee JT, Rittberg BR and Adson DE. Weight Loss During Chronic, Cervical Vagus Nerve Stimulation in Depressed Patients with Obesity: An Observation, International Journal of Obesity, 31, 1756-1759 (2007).

First MB, Spitzer RL, Williams JBW, Gibbon M. *Structured Clinical Interview for DSM-IV*. Clinician Version. Administration Booklet (88 pp.). American Psychiatric Association: Washington, DC 1997.

Hamilton M. A rating scale for depression. *J Neuro Neurosurg Psychiatry* 1960; 23: 56-62.

Rush AJ, Marangell LB, Sackheim HA, George MS, Brannan SK, Davis SM et al. Vagus nerve stimulation for treatment-resistant depression: a randomized controlled acute phase trial. *Biol Psychiatry* 2005; 58: 347-354.

Peters JH, McKay BM, Simasko SM, Ritter RC. Leptin-induced satiation mediated by abdominal vagal afferents. *Am J Physiol Regul Integr Comp Physiol* 2005, 288: R879-R884.

Stephan E, Pardo JV, Faris PL, Hartman BK, Kim SW, Ivanov EH et al. Functional neuroimaging of gastric distention. *J Gastrointest Surg* 2003; 7: 740-749.

Sobocki J. Fourtanier G, Estany J, Otal P. Does vagal stimulation affect body composition and metabolism? Experimental study of a new potential technique in bariatric surgery. *Surgery* 2006; 139: 209-216.

Ferrari B, Arnold M, Carr RD, Langhans W, Pacini G, Bódvarsdottir TB et al. Subdiaphragmatc vagal deafferetation affects body weight gain and glucose metabolism in obese male Zucker (fa/fa) rats. *Am J Physiol Regul Integr Comp Physiol* 2005; 289: R1027-R1034.

Kreier F, Fliers E, Voshol PJ, Van Eden CG, Havekes LM, Kalsbeek A et al. Selective parasympathetic innervation of subcutaneous and intra-abdominal fat—functional implications. *J Clin Invest* 2002; 110: 1243-1250.

Fallen EI. Vagal afferent stimulation as a cardioprotective strategy? Introducing the concept. *Ann Noninvasive Electrocardiol* 2005; 10: 441-446.

Uno K, Katagiri H, Yamada T, Ishigaki Y, Ogihara T, Imai J et al. Neuronal pathway from the liver modulates energy expenditure and systemic insulin sensitivity. *Science* 2006; 312: 1656-1659.

Burneo JG, Faught E, Knowlton R, Morawetz R, Kuznieky R. Weight loss associated with vagas nerve stimulation. *Neurology* 2002; 59: 463-464.

Schauer PR, Ikramuddin S. Laparoscopic surgery for morbid obesity. *Surg Clin N Am* 2001; 81: 1145-1179.

Saber AA. Gastric pacing: a new modality for the treatment of morbid obesity. *J Invest Surg* 2004; 17: 57-59.

Rush AJ, Sackeim HA, Marangell LB, George MS, et al. Effects of 12 Months of Vagus Nerve Stimulation in Treatment-Resistant Depression: A Naturalistic Study. *Biol Psychiatry* 2005;58:355-363.

Rush AJ, Marangell LB, Sackeim HA, George MS, Brannan SK, Davis SM, Howland R, Kling MA, Rittberg BR, Burke WJ, Rapaport MH, Zajecka J, Nierenberg AA, Husain MM, Ginsberg D and Cooke RG. Vagus Nerve Stimulation for treatment-Resistant Depression: A Randomized, Controlled Acute Phase Trial. Biol Phychiatry 2005; 58:347-354 (2005 Society of Biological Psychiatry).

Mayberg, HS, Brannan SK, Mahurin RK, Jerabek PA, Brickman JS, Tekell JL, Silva JA, McGinnis S, Glass TG, Martin CC and Fox PT. Cingulate function in depression: a potential predictor of treatment response. Clinical Neuroscience and Neuropathology NeuroReport vol. 8, No. 4, 1057-1061 (Mar. 3, 1997).

Ko D, Heck C, Grafton S, Apuzzo MLJ, Couldwell, WT, Chen T, Day JD, Zelman V, Smith TR and DeGiorgia CM. Vagus Nreve Stimulation Activates Central Nervous System Structures in Epileptic Patients During PET H2 15O Blood Flow Imaging. Neurosurgery. vol. 39(2), pp. 426-431, Aug. 1996 (9 pages).

Henry TR, Votaw JR, Pennell PB, Epstein CM, Bakay RAE, Faber TL, Grafton ST and Hoffman JM. Acute blood flow changes and efficacy of vagus nerve stimulation in partial epilepsy. Neurology. vol. 52(6) pp. 1166-1173. Apr. 12, 1999 (21 pages).

Vonck K, Boon, P, Laere KV, D'Have M, Vandekerckhove T, O'Connor S, Brans BN, Dierckx R and De Reuck J. Acute Single Photon Emission Computed Tomographic Study of Vagus Nerve Stimulation in Refractory Epilepsy. *Epilepsia*, 41(5):601-609, 2000.

Zald DH and Pardo JV. The Neural Correletates of Adversive Auditory Stimulation. NeuroImage 16, 746-753 (2002).

Zald DH and Pardo JV. Functional neuroimaging of the olfactory system in humans. International Journal of Psychophysiology 36 (2000) 165-181.

Zald DH, Lee JT, Fluegel KW and Pardo JV. Aversive gustatory stimulation activates limbic circuits in humans. *Brain* (1998), 121, 1143-1154.

Zald DH and Pardo JV. Cortical Activation Induced by Intraoral Stimulation with Water in Humans. Chem. Senses 25: 267-275, 2000.

Zald DH, Hagen MC and Pardo JV. Neural Correlates of Tasting Concentrated Quinine and Sugar Solutions. *J Neurophysiol* 87: 1068-1075, 2002.

Henry TR, Bakay RAE, Votaw JR, Pennell PB, Epstein CM, Faber TL, Grafton ST and Hoffman JM. Brain Blood Flow Alterations Induced by Therapeutic Vagus Nerve Stimulation in Partial Epilespy: I. Acute Effects at High and Low Levels of Stimulation. *Epilepsia*, 39(9): 983-990, 1998.

Rush AJ, George MS, Sackeim HA, Marangell LB, Husain MM, Giller C, Nahas Z, Haines S, Simpson, Jr. RK and Goodman R. Vagus Nerve Stimulation (VNS) for Treatment-Resistant Depressions: A Multicenter Study. Biol Psychiatry 2000; 47:276-286.

* cited by examiner

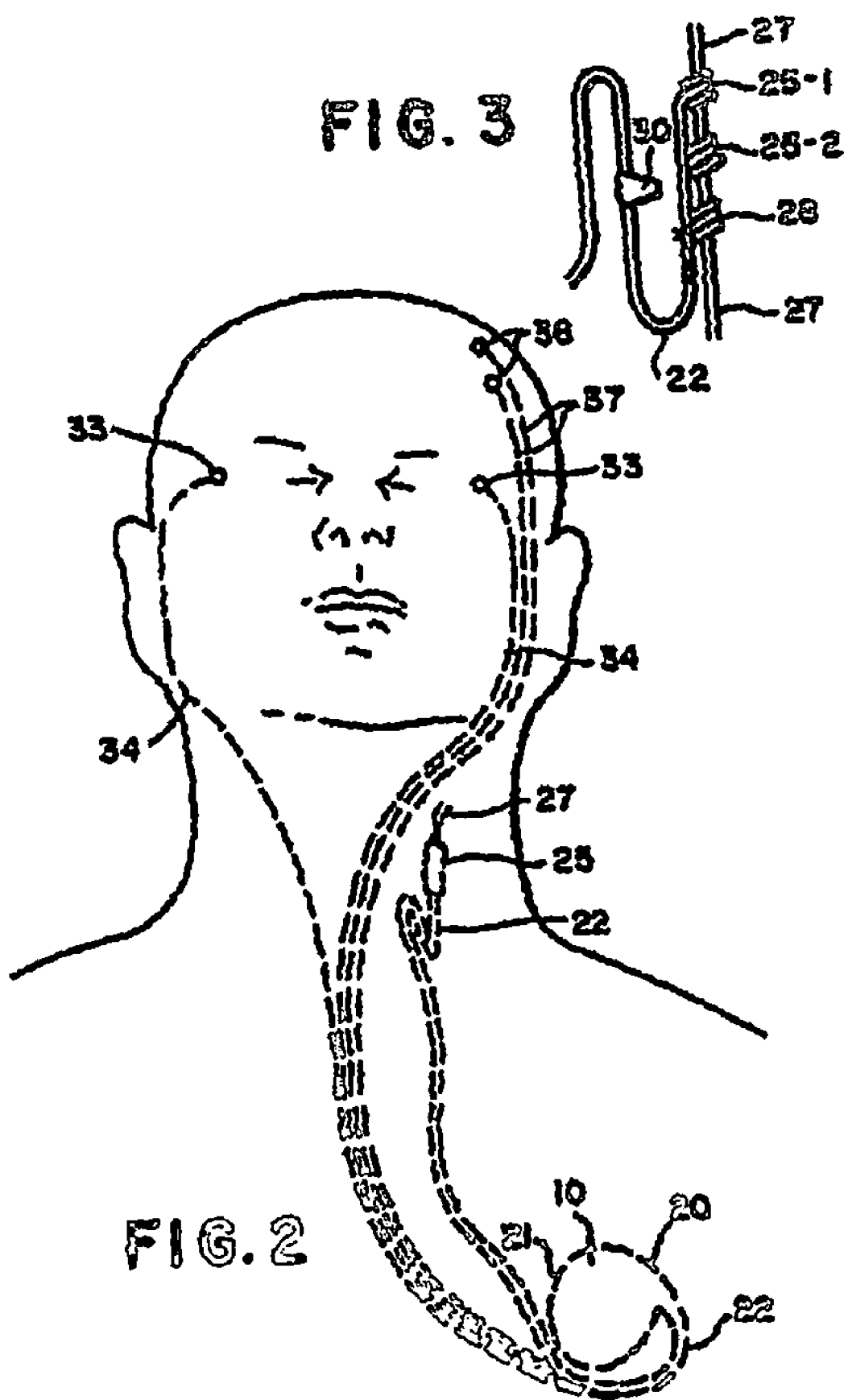

CERVICAL VAGAL STIMULATION INDUCED WEIGHT LOSS

This application claims the benefit of U.S. Provisional Patent Application No. 60/439,824 filed Jan. 14, 2003, the entirety of which is hereby incorporated herein by reference for all purposes.

FIELD OF THE INVENTION

The present invention relates to a novel method for inducing weight loss in a patient by stimulating the vagus nerve in the patient's neck.

BACKGROUND OF THE INVENTION

Obesity is a major public health concern afflicting 300 million people worldwide. Serious and common complications from obesity include hypertension, diabetes, cardiovascular disease, dyslipidernia, osteoartbritis, sleep apnea, etc. Standard treatments include diet, exercise, behavioral therapy, and medications. Most patients do not succeed at maintaining normal weight. In some with disabling and life-threatening obesity, gastric surgery provides a last resort, despite invasiveness, potential for serious complications, and cost. More effective and novel approaches to the treatment of obesity are needed. One largely untapped focus is the brain itself.

In animal studies, stimulation of the vagus nerve in the abdomen of healthy male rabbits, by electrical pacing during a month, reduces food intake and body mass. Sobocki. J., et al., Microchip vagal pacing reduces food intake and body mass. *Hepatogastroenterology* 48:1783-1787 (2001). Stimulation of the human vagus nerve to treat eating disorders also has been described. See, for instance, U.S. Pat. No. 6,609,025 ("the '025 patent") to Barrett et al., assigned to Cyberonics, Inc., and patents discussed therein.

U.S. Pat. No. 5,263,480 to J. Wernicke et al. ["the '480 patent," which issued on application Ser. No. 07/926,915, filed Aug. 7, 1992, which was a continuation of application Ser. No. 07/649,618 of the same inventors filed Feb. 1, 1991, now U.S. Pat. No. 5,188,104], assigned to the same assignee as [Barrett et al.], discloses treatment for eating disorders including obesity and compulsive overeating disorder by selectively applying modulating electrical signals to the patient's vagus nerve, preferably using an implanted neurostimulator. Modulating signals may be used to stimulate vagal activity to increase the flow of neural impulses up the nerve, or to inhibit vagal activity to block neural impulses from moving up the nerve, toward the brain, for producing excitatory or inhibitory neurotransmitter release.

Barrett et al. in the '025 patent further characterize the teachings of the '480 patent as follows:

Both of these cases of modulating the electrical activity of the vagus nerve have been termed vagus nerve stimulation, or VNS. The '480 patent theorized that VNS could be used for appetite suppression by causing the patient to experience satiety, a sensation of 'fullness' of the stomach which would result in decreased food consumption and consequent weight reduction. For example, the stimulus generator of the neurostimulator is implanted in a convenient location in the patient's body, attached to an electrical lead having a nerve electrode implanted on the vagus nerve or branch thereof in the esophageal region slightly above the stomach. If the patient's food consumption over a given period exceeded a predetermined threshold level, detected and measured for example by sensing electrodes implanted at or near the esophagus, the stimulus generator is triggered to apply VNS and thereby normal waking hours except in periods of prescribed mealtimes, or is applied as a result of patient intervention by manual activation of the stimulus generator using external magnet control.

Barrett et al. in the '025 patent also characterize the disclosure of U.S. patent application Ser. No. 09/346,396 ("the '396 application," filed Jul. 1, 1999 (now U.S. Pat. No. 6,587,719 to Barrett et al., also assigned to Cyberonics, Inc.), as follows:

The aforementioned '396 application discloses a method of treating patients for obesity by bilateral stimulation of the patient's vagus nerve (i.e., bilateral VNS) in which a stimulating electrical signal is applied to one or both branches of the vagus. The parameters of the signal are predetermined to induce weight loss of the patient. The signal is preferably a pulse signal applied at a set duty cycle (i.e., its on and off times) intermittently to both vagi. In any event, VNS is applied at a supra-diaphragmatic position (i.e., above the diaphragm) in the ventral cavity. The electrical pulse stimuli are set at a current magnitude below the retching level of the patient (e.g., not exceeding about 6 milliamperes (mA), to avoid patient nausea) in alternating periods of continuous application and no application. Pulse width is set at or below 500 microseconds (µs), and pulse repetition frequency at about 20-30 Hz. The on/off duty cycle (i.e., first period/ second period of the alternating periods) is programmed to a ratio of about 1:1.8. The neurostimulator, which may be a single device or a pair of devices, is implanted and electrically coupled to lead(s) having nerve electrodes implanted on the right and left branches of the vagus.

[i]n dog tests conducted by the applicants herein, the dietary pattern included twice-a-day feedings of approximately 400 grams of solid food with one scoop of soft meat product added to make the food more edible. During the surgical procedure, a threshold referred to herein as the retching threshold was documented while the animal was under anesthesia, based on the threshold value of the stimulus output current of the device at which the animal exhibited a retching or emetic response. The amount of current was adjusted to determine this threshold. Other parameters were left fixed at a frequency of 30 Hertz (Hz), a pulse width of 500 milliseconds (ms), and an on/off cycle of one minute on and 1.8 minutes off.

Barrett et al. in the '025 patent disclose yet another variation of treatment of obesity by vagus nerve stimulation, using bilateral sub-diaphragmatic stimulation, which the '025 patent characterizes as follows:

According to the present invention, a method of treating patients for obesity comprises unilateral or bilateral stimulation of the left and right vagi at a sub-diaphragmatic position (i.e., below the diaphragm) in the ventral cavity, rather than at a supra-diaphragmatic position as taught by the '396 application. The stimulating electrical signal is preferably applied to the vagus two to three inches below the diaphragm, and may be applied either synchronously or asynchronously to both the right and left branches, preferably in the form of a series of pulses applied intermittently to both branches according to a predetermined on/off duty cycle. The intermittent application is preferably chronic, rather than acute. However, continuous application or acute application by bilateral stimulation of the right and left vagi or unilateral contemplated.

The sub-diaphragmatic application of VNS may have an enhanced effect in inducing satiety in the patient, being in closer proximity to the stomach itself. Certainly, in the case of neurostimulator device implantation superficially in the abdominal region of the patient, the sub-diaphragmatic application has an advantage of enabling shorter leads for the nerve electrode(s). Additionally, application of the neurostimulator may be more easily accomplished with this approach as opposed to a supra-diaphragmatic approach which requires accessing the vagi in the chest cavity.

Accordingly, as taught, for instance, by Barrett et al. in the '025 patent, above, implantation of the devices used to provide the electrical pulses to the vagus nerve in abdomen, or supradiaphragmatically or sub-diaphragmatically, typically requires an invasive implantation procedure exposing the patient to risks associated with such invasive procedures. Thus, methods of inducing weight loss in a patient that do not require such invasive surgical implantation procedures are desired.

In addition, none of the patents discussed by Barrett et al. in the '025 patent, nor the '025 patent itself, discloses any clinical results of testing the disclosed methods on human subjects. Greene et al., Perspectives on the metabolic management of epilepsy through dietary reduction of glucose and elevation of ketone bodies, *J. Neurochem.* 86:529-537 (2003), discloses (at p. 533) that vagal nerve stimulation is a novel therapy that significantly reduces seizure frequency in patients with refractory seizures and asserts that "(the vagus nerve is also known to affect eating behavior and vagal nerve stimulation has been used to treat morbid obesity (Roslin and Kurian 2001)", where the full citation for the disclosure of "Roslin and Kurian 2001" is given as "Roslin M. and Kurian M. (2001) The use of electrical "Roslin M" is presumably Mitchell S. Roslin, one of the inventors of the '025 patent.

The above cited publication by Roslin and Kurian (*Epilepsy Behav.* 2, S11-S16, 2001) teaches that

[o]besity is actually defined as having excess adiposity or fat tissue. Since it is more practical to measure height and weight rather than amount of fat, determination of level of obesity is generated using these numbers. The most accurate numerical assessment is obtained by determining the body mass index (BMI). This number is derived by dividing weight in kilograms (or pounds) by height in meters squared (or feet). A BMI of more than 40 is considered morbidly obese. As an example, an individual who is 5 feet 10 inches tall (177.8 cm) and weighs 280 pounds (127 kg) has a body mass index of 40. A patient with a BMI of 25 to 30 is considered overweight; 30 to 35 corresponds to stage I obesity, 35 to 40 to stage II obesity, and >40 to stage III or morbid obesity.

Roslin and Kurian further disclose the basis for their approach toward developing a method of treating obesity using VNS, as follows:

The combination of the anatomic relationship of the vagus nerve to the GI tract and the above physiologic experiments provided the rationale for the investigation of electrical stimulation of the vagus nerve for obesity and development of a preclinical animal experimental program. Despite this appealing theory, one major factor needed to be considered prior to beginning investigation. During the numerous years of clinical experience with vagus nerve stimulation (VNS) for epilepsy, no weight loss was reported, other than a few anecdotal reports. Thus several modifications were necessary. Because we would be best to be in closer proximity to the gastroesophageal junction. Such positioning would avoid stimulation of fibers that join the trunk from the heart and lungs and, we speculated, have a greater likelihood of stimulating our target fibers. Additionally, positioning away from the neck and the recurrent laryngeal nerve would allow the delivery of higher levels of current that could be necessary to stimulate these unmyelinated fibers. Finally, because the right and left trunks have different distributions in the abdomen and the contribution of both could be essential, we chose to investigate bilateral stimulation of the vagus nerve.

Following a preclinical study which Roslin and Kurian considered to study suggest that the use of bilateral VNS is effective in changing eating behavior, with a corresponding weight loss in a canine animal model, the authors describe the initiation of a human "pilot" program, as follows:

The results of the canine study and the known safety of VNS in humans served as the basis for initiating a phase I study. Enrollment began during the summer of 2000, and clinical implantation has started. Thirty patients will be enrolled, all of whom will have their generators activated. To control for placebo, 60% of the patients will have their NCP systems activated 2 weeks after surgery, and those of the other 40% will be activated 14 weeks after surgery. Initial implantation has been performed with an open technique to ensure proper lead placement. Laparoscopic and thoracoscopic techniques will be used in future implants. Because obesity is a chronic disease, long-term data are mandatory before results can be analyzed. Preliminary data may be available late in 2001.

experience with vagus nerve stimulation (VNS) for epilepsy, the disclosure of Roslin and Kurian contemplates a need to stimulate the small unmyelinated C fibers of the nerve and, hence, that VNS stimulation for treating obesity would best be in closer proximity to the gastroesophageal junction, thereby avoiding stimulation of fibers that join the trunk from the heart and lungs and allowing the delivery of higher levels of current that could be necessary to stimulate these unmyelinated fibers. Finally, because the right and left trunks have different distributions in the abdomen and the contribution of both could be essential, these authors chose to investigate bilateral stimulation of the vagus nerve in an animal model and thereafter in human clinical testing.

U.S. Pat. No. 6,611,715 ("the '715 patent") to Boveja, issued Aug. 26, 2003, discloses apparatus and methods for neuromodulation therapy for obesity and compulsive eating disorders using an implantable lead-receiver and an external stimulator. According to Boveja in the '715 patent:

[a]system and method of neuromodulation adjunct (add-on) therapy for obesity and compulsive eating disorders, comprises an implantable lead-receiver and an external stimulator. Neuromodulation is performed using pulsed electrical stimulation. The external stimulator contains a power source, controlling circuitry, a primary coil, and predetermined programs which control the different levels of therapy. The primary coil of the external stimulator inductively transfers electrical signals to the lead-receiver, which is also in electrical contact with the left vagus nerve. The external stimulator emits electrical pulses to stimulate the vagus nerve according to a predetermined program. In a second mode of operation, an operator may manually override the predetermined sequence of stimulation. The protected. The external stimulator may also be equipped with a telecommunications module to control the predetermined programs remotely.

Further according to Boveja in the '715 patent:

Apparatus and method for neuromodulation, in the current application has several advantages over the prior art implantable pulse generator. The external stimulator described here can be manufactured at a fraction of the cost of an implantable pulse generator. The therapy can be freely applied with [sic, without] consideration of battery depletion. Surgical replacement of pulse generator is avoided. The programming is much simpler, and can be adjusted by the patient within certain limits for patient comfort. And, the implanted hardware is significantly smaller.

U.S. Pat. No. 6,449,512 ("the '512 patent") to Boveia, issued Sep. 10, 2002, discloses apparatus and methods for treatment of urological disorders using a "programmerless" implantable pulse generator system, which is characterized as follows:

System and method of neuromodulation therapy for urinary incontinence disorders comprises a lead to selectively stimulate the sacral plexus and an implantable pulse generator for providing the appropriate pulses. The implantable pulse generator having prepackaged/predetermined programs stored in the memory of the pulse generator, and means for accessing these with an external magnet. The pulse generator adapted to selectively activate predetermined programs with the external magnet, thereby eliminating the need for an external programmer. The elimination of the external programmer resulting in significant cost reduction with essentially the same functionality.

vagus nerve stimulation, *Neurology* 59:463-464 (2002) reported on weight loss in patients who underwent VNS implantation for treatment of epilepsy for up to two years, as follows:

Of the 27 patients for who complete data were available, 17 had lost weight. Weight in the remaining patients fluctuated, without a specific pattern toward weight gain.

Eight patients (25%) (four men, age range 18-41) had significant weight loss of more than 5% of body weight, and of these, five lost more than 10% of body weight. Two patients lost more than 5% of the weight in the first 6 months, four at 1 year, and six in 2 year. More than 10% of weight loss was seen in one patient after 6 months, in two patients after 1 year, and in three patients after 2 years of VNS (figure [captioned ""Percentage of weight loss vs months of follow-up for each patient found with this characteristic side effect."]). In none of our patients was VNS discontinued or the generator removed due to weight loss.

Burneo et al. concluded that,

"[a]lthough weight loss may be multifactorial, its occurrence in our patients undergoing VNS implantation appears causally related. This may be due to decreased appetite, resulting in changes in eating behaviors, or to gastrointestinal side effects, such as dyspepsia, previously reported as a side effect of VNS [citations omitted]. Even though this was not a control-case study, patients and physicians should be aware of weight loss as an associated phenomenon of VNS stimulation."

Accordingly, the report of Burneo et al. does not disclose whether the patients who lost weight in this epilepsy study were obese or of normal weight and does not teach or suggest should be aware of weight loss as an associated phenomenon [or "characteristic side effect"] of VNS stimulation."

It is known that, in the human body the innervation of the right and left vagus nerves is different. The innervation of the right vagus nerve is such that stimulating it results in profound bradycardia (slowing of the heart rate). The left vagus nerve has some innervation to the heart, but mostly innervates the visceral organs such as the gastrointestinal tract. It is further known that stimulation of the left vagus nerve does not cause substantial slowing of the heart rate or cause any other significant deleterious side effects.

SUMMARY OF THE INVENTION

The present invention is based in part on the surprising observation by the inventors that chronic cervical vagus nerve stimulation (cVNS) of the left vagal trunk for extended periods of time, under conditions similar to those used for treatment of epilepsy, effected a consistent and reliable reduction of weight, as described herein below. Weight loss occurred gradually over one year and some of the most obese patients continued to lose weight thereafter. The amount of weight loss was proportional to the initial severity of the obesity.

Accordingly, the present invention relates to methods of inducing weight loss in patients through the stimulation of the vagus nerve in the patient's neck. In one embodiment an obese patient is treated with chronic vagus nerve stimulation in the neck until the patient achieves and maintains an amount of weight loss appropriate for such patient. In one embodiment, a neurostimulator (preferably but not necessarily implantable) is employed to deliver electrical impulses to the vagus nerve either unilaterally to one branch or bilaterally to both branches of the vagus nerve simultaneously or alternately. In some embodiments, the method of the invention is used to treat obesity in patients, without regard to whether the obesity is related to a compulsive eating disorder.

obesity in a patient comprising chronic cervical vagus nerve stimulation (cVNS) with an electrical signal applied directly or indirectly to the vagus nerve in the neck of the patient. In some embodiments this method comprises unilateral stimulation of the trunk of the left vagus nerve in the neck of the patient Some embodiments of this method further comprise implanting subcutaneously within the patient a signal generator operably coupled to one end of an electrical lead that is operably coupled at the other end to the vagus nerve for generating and applying the electrical signal to the vagus nerve. Advantageously, the signal generator used in the invention method is implanted under the skin of the chest of the patient but also may be implanted under the skin of the neck or the upper arm of the patient.

In this method, the electrical signal may be applied for a substantially continuous period of at least six months and, preferably, the electrical signal is applied for a substantially continuous period of greater than two years. Further, the electrical signal may have at least one variable parameter selected from the group consisting of current amplitude, pulse width, pulse frequency, and a duty cycle of alternating intervals with power on and power off. In particular embodiments, the electrical signal may have an output current amplitude between about 0.5 mA to about 1.5 mA, a stimulation frequency between about 10 Hz and 100 Hz, a pulse width in the range of 100 microseconds to 1000 microseconds (μs), and a duty cycle of intervals with power on for about 10 s to about 100 s and power off for the remainder of each 3 minute to 10 minute period of treatment. Advantageously, the electrical signal has an output current amplitude of about 0.75 mA, a stimulation frequency of about 30 Hz, a pulse width of either about 250 microseconds or about 500 microseconds (μs), and a duty cycle intervals with power on for about 30 s and power off for the remainder of each 5 minute period of treatment.

index, BMI) proportional to the weight (BMI) of the patient at the beginning of treatment The method also generally produces weight loss only in obese patients. Advantageously, therefore, the method is helpful for a patient having a body mass index (BMI) greater than 25, greater than 30, or even greater than 40. As noted above, a patient with a BMI of 25 to 30 is considered overweight; 30 to 35 corresponds to stage I obesity, 35 to 40 to stage II obesity, and over 40, to stage III or morbid obesity.

In another aspect the invention provides a method of treating obesity in a patient which comprises implanting subcutaneously within the patient a device comprising an electrical signal generator and at least one electrical lead having at least one proximal electrical connector and one distal nerve electrode. This method further comprises operably connecting a proximal electrical connector of the electrical lead to the signal generator, either before or after implanting the signal generator or the lead, and operably coupling a distal nerve electrode of the electrical lead to the trunk of the left vagus nerve in the neck of the patient. The method then involves activating the signal generator to chronically stimulate the vagus nerve with an electrical signal, advantageously for a period of at least one year.

This method of the invention utilizes an implantable pulse generator system similar to that described in U.S. Pat. No. 6,449,512 Boveja for treatment of urological disorders, which has been called a "programmerless" pulse generator system. This implantable pulse generator comprises prepackaged/predetermined programs stored in a memory component of the pulse generator, and an external control system for accessing these with an external control element, such as a magnet. In particular, the electrical signal used in the present invention method typically has at least one variable parameter selected from the group consisting of current amplitude, pulse width, pulse frequency, and a duty cycle of alternating intervals with power on and power off. The device also further comprises at least two predetermined programs for that cannot be altered while the device is implanted in the patient. Further, the signal generator is activated by an externally activated control system that selectively activates each of the predetermined programs, whereby the implanted device provides vagus nerve stimulation which is controllable by the externally activated control system.

In various embodiments the externally activated control system of the invention may be a magnetically activated control system, a mechanically activated control system that responds to tapping on the skin near the device, or an acoustically activated control system that responds to an audio or supersonic signal. Examples of systems suitable for use as externally activated control systems in the present invention are disclosed, for instance, in U.S. Pat. No. 5,722,998 to Prutchi et al., which discloses an implantable medical device with a sensor to detect the presence of a magnet in order to command the device to enter a predetermined mode of operation, and U.S. Pat. No. 5,304,206 to Baker, Jr. et al., which discloses other suitable external activation techniques for an implantable medical device.

Advantageously, in the method using by an externally activated control system that selectively activates each of the predetermined programs, such programs control parameters of the electrical signal such that the output current amplitude is between about 0.5 mA to about 1.5 mA, stimulation frequency is between about 10 Hz and 100 Hz, pulse width is in the range of 100 microseconds to 1000 microseconds (µs), and the duty cycle has intervals with power on for about 10 s to about 100 s and power off for the remainder of each 3 minute to 10 minute period of treatment. In particular, advantageously at least one of the predetermined programs to control parameters of the electrical signal produces an electrical signal having an output current of about 0.75 mA, a stimulation frequency of about 30 Hz, a pulse width of either about 250 microseconds or about 500 microseconds (µs), and a duty cycle of intervals treatment.

Another aspect of the present invention relates to apparatus for treating obesity in a patient, comprising a device suitable for implanting subcutaneously in the patient and at least one implantable electrical lead. The device comprises an electrical signal generator, and the electrical lead has at least one proximal connector for operably coupling the electrical lead to the signal generator and at least one distal nerve electrode for operably connecting the electrical lead to a trunk of the vagus nerve in the neck of the patient. Advantageously, the signal generator comprises a power source suitable for chronically stimulating the trunk of the vagus nerve with an electrical signal while implanted for a period of at least one year, more preferably for at least two years, or three years or longer.

In this apparatus, the electrical signal produced by the signal generator of the invention device has at least one variable parameter selected from current amplitude, pulse width, pulse frequency, and a duty cycle of alternating intervals with power on and power off, and the device further comprises a memory component containing at least two predetermined programs for controlling at least one parameter of the electrical signal according to a programmed regimen. For reasons of simplicity and attendant economy, the implantable device is designed without any capability for altering the electrical signal parameter regimen specified in each predetermined program while the device is implanted in the patient. However, the signal generator is designed to be activated by an externally activated control system that selectively activates each of the predetermined programs, thereby allowing the apparatus to provide chronic cervical vagus nerve stimulation which is controllable by the externally activated control system, such as a magnetically activated control system, a mechanically activated control system, or an activation system responsive to an audio or supersonic signal. Typically, the predetermined programs controlling the electrical signal between about 10 Hz and 100 Hz, a pulse width in the range of 100 microseconds to 1000 microseconds (µs), and a duty cycle of intervals with power on for about 10 s to about 100 s and power off for the remainder of each 3 minute to 10 minute period of treatment.

Various other features, objects and advantages of the invention will be made apparent from the following description taken together with the drawings.

BRIEF DESCRIPTION OF THE DRAWINGS

FIG. 2 is a simplified fragmentary illustration of one embodiment of the stimulus generator and lead/electrode system of the neurostimulator implanted in the patient's body (adapted from FIG. 2 of U.S. Pat. No. 5,299,569 to Wernicke et al.);

FIG. 3 is a detailed fragmentary illustration of the nerve electrode as implanted on the vagal nerve in the neck of the patient for modulating vagal activity (adapted from FIG. 3 of U.S. Pat. No. 5,299,569 to Wernicke et al.);

DETAILED DESCRIPTION OF THE INVENTION

Figure 1:
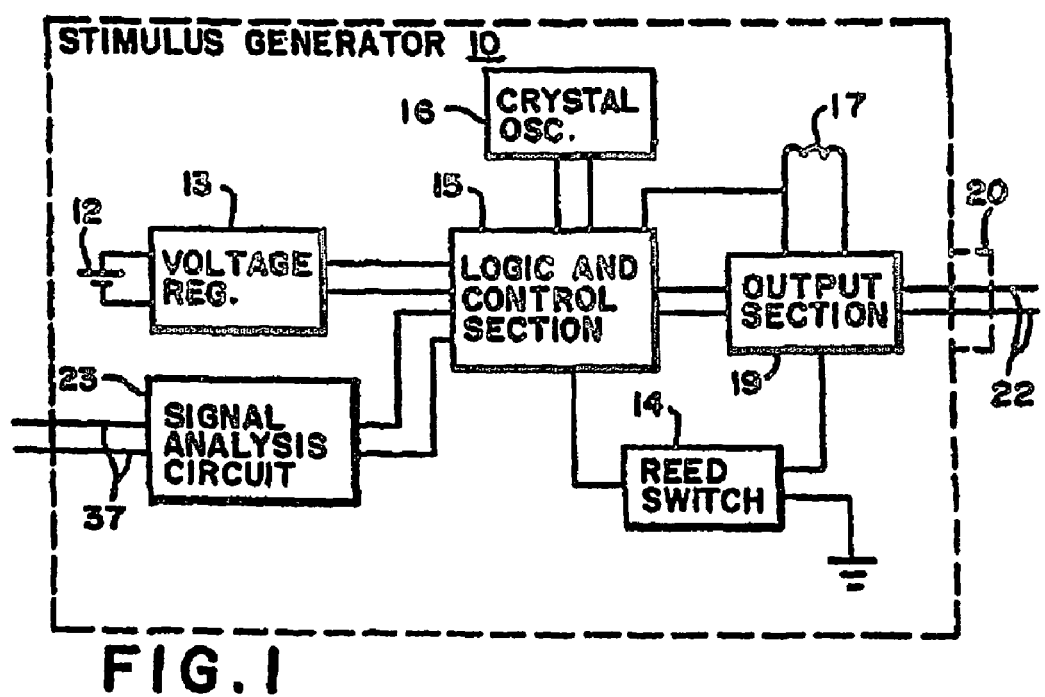
FIG. 1 is a simplified block diagram of an implantable neurostimulator electronics package (stimulus generator) for use (with appropriate parameter settings and ranges) in treating patients to induce weight loss according to the present invention (adapted from FIG. 1 of U.S. Pat. No. 5,299,569 to Wernicke et al., the disclosure of which is hereby incorporated herein by reference in its entirety)

Referring now to the drawings, a block diagram of the basic components of the stimulus generator of a neurostimulator and their interrelationship is illustrated in FIG. 1, and further details of location of an implantable version of the device and the associated lead/electrode system are shown in FIGS. 2 and 3. A generally suitable form of neurostimulator for use in the apparatus of the present invention is disclosed in U.S. patent application Ser. No. 07/434,985, now U.S. Pat. No. 5,154,172, issued Oct. 13, 1992, to Anthony J. Varrichio et al., titled "Current Source with Programmable Overhead Voltage" (referred to herein as the '985 application"). The specification of the '985 application is incorporated herein in its entirety by reference.

The neurostimulator useful with the method of the invention utilizes a conventional microprocessor and other standard electrical and electronic components, and in the case of an implanted device, communicates with a programmer and/or monitor located external to the patient's body by asynchronous serial communication for controlling or indicating states of the device. Passwords, handshakes and parity checks may be employed for data integrity.

battery operated device and especially so where the device is implanted for medical treatment of a disorder, and means for providing various safety functions such as preventing accidental reset of the device.

The stimulus generator 10 (FIG. 1) is preferably adapted to be implantable in the patient's body, in a pocket formed by the surgeon just below the skin in the chest as shown in FIG. 2. Although a primarily external neurostimulator may alternatively be employed. The neurostimulator also includes implantable stimulating electrodes (described below) together with a lead system 22 for applying the output signal of the stimulus generator to the patient's vagus nerve. Components external to the patient's body may include a programming wand for telemetry of parameter changes to a stimulus generator so signals from the generator may be monitored, and a computer and associated software for adjustment of parameters and control of communication between the generator, the programming wand and the computer. Such external components of the system are not shown in the drawings. The device of the invention may include an internet transmitting/receiving device that will allow parameters and monitoring information to be transmitted through the internet to/from a remote site.

In conjunction with its microprocessor-based logic and control circuitry, the stimulus generator 10 or other implanted or external circuitry may include detection circuitry for sensing an event indicative of an abnormality to trigger automatic delivery of the stimulating signal. For example, surface or depth electrodes may be implanted to sense specific characteristics of the patient's EEG for triggering the therapy. However, this involves complex and delicate electrode/lead implantation procedures as well as the requirement of circuitry for spectral analysis and/or programmable spectral or pattern recognition. Preferably, therefore, the treatment is applied continuously, periodically or intermittently or in accordance with the patient's circadian rhythm.

FIG. 1, for use in treating patients to induce weight loss according to the present invention without a signal analysis circuit which is not needed for embodiments in which no sensory input signal is monitored.

Figure 4:
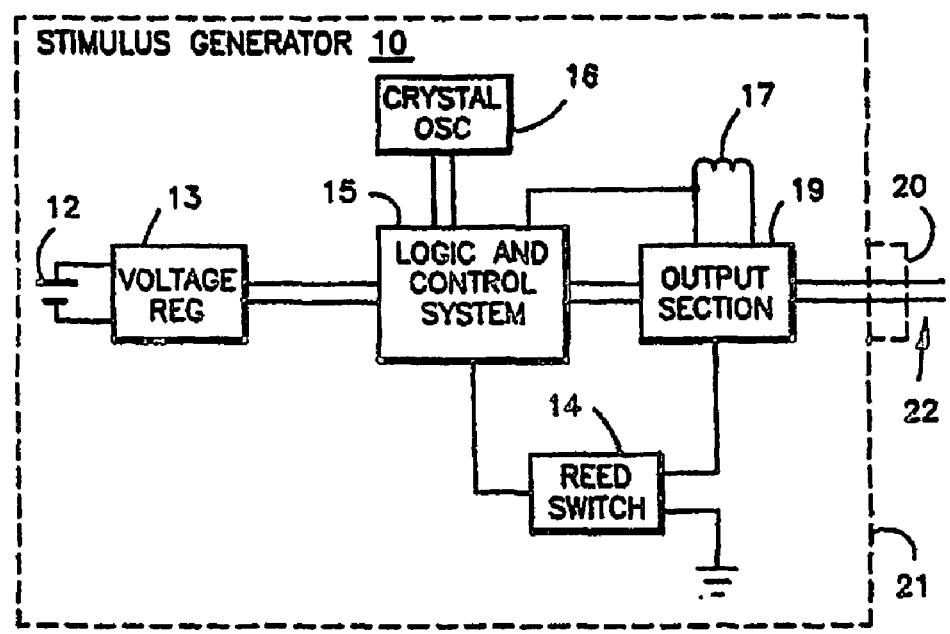
FIG. 4 is a simplified block diagram of an implantable neurostimulator electronics package (stimulus generator) for use (with appropriate parameter settings and ranges) in treating patients to induce weight loss according to the present invention (adapted from FIG. 1 of U.S. Pat. No. 5,330,513 to Wernicke et al., the disclosure of which is hereby incorporated herein by reference in its entirety), which is simpler than the stimulus generator in FIG. 1, above, because it has no signal analysis circuit which is not needed for embodiments in which no sensory input signal is monitored.
Figure 5:
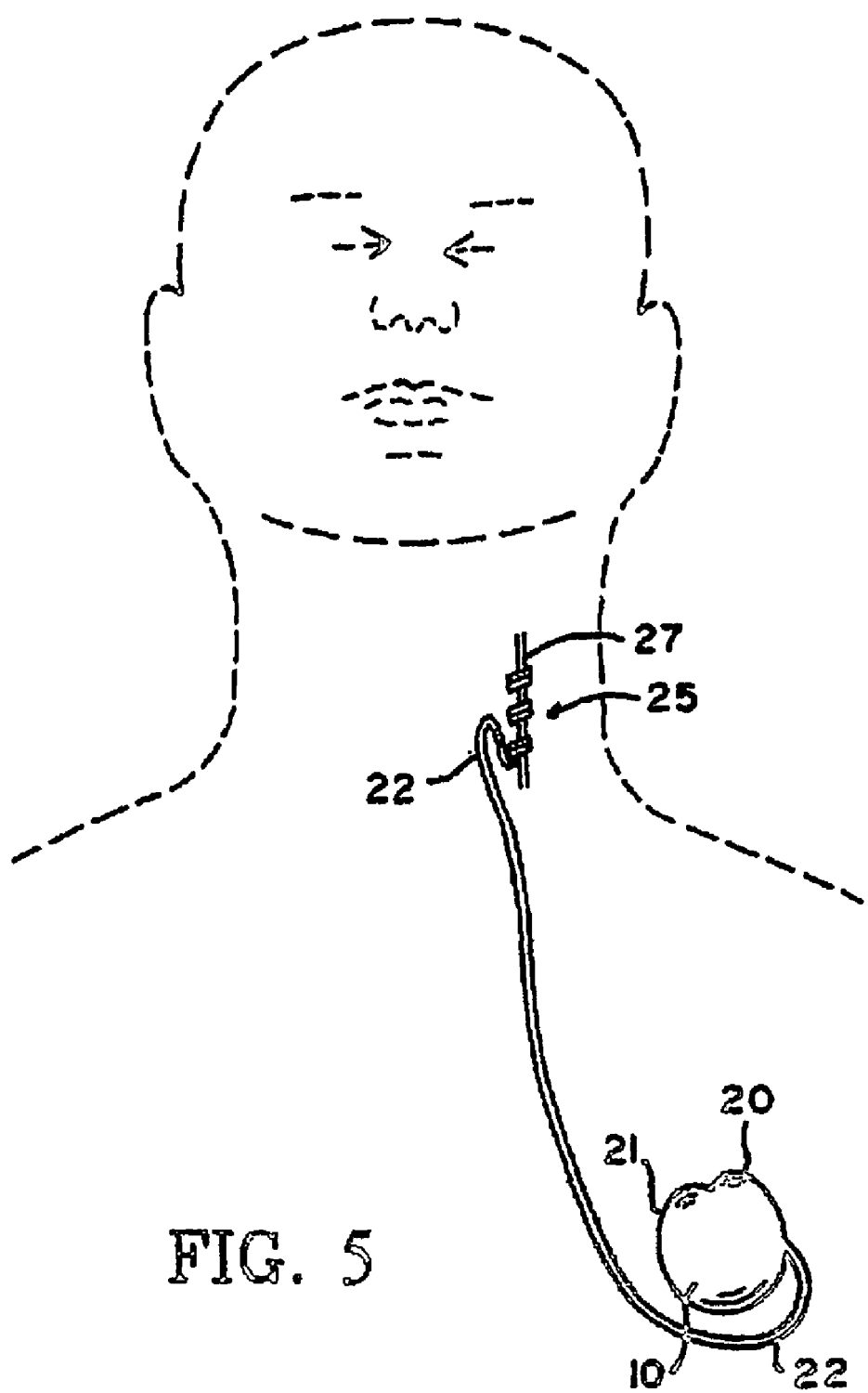
FIG. 5 is a simplified fragmentary illustration of a preferred embodiment of the stimulus generator and lead/electrode system of the neurostimulator implanted in the patient's body (adapted from FIG. 2 of U.S. Pat. No. 5,330,513 to Wernicke et al.), showing implantation and wiring of the stimulus generator in FIG. 4, above, to stimulate the left vagus nerve only, with no sensory input leads.

As shown in FIG. 1 and FIG. 4, stimulus generator 10 includes a battery (or set of batteries) 12, which may be of any reliable long-lasting type conventionally employed for powering implantable medical electronic devices (such as batteries employed in implantable cardiac pacemakers or defibrillators). In the preferred embodiment of the stimulus generator, the battery is a single lithium thionyl chloride cell. The terminals of the cell 12 are connected to the input side of a voltage regulator 13. The regulator smoothes the battery output to produce a clean, steady output voltage, and provides enhancement thereof such as voltage multiplication or division if necessary for a specific application.

Regulator 13 supplies power to logic and control section 15, which includes a microprocessor and controls the programmable functions of the device. Among these programmable functions are output current, output signal frequency, voltage, output signal pulse width, output signal on-time, output signal off-time, daily treatment time for continuous or periodic modulation of vagal activity, and output signal-start delay time. The device may use either one of these programmable functions independently or for a particular patient, a combination of parameters may be used. Such programmability allows the output signal to be selectively crafted for application to the stimulating electrode set (FIGS. 2 and 3) to obtain the desired modulation of vagal activity for treatment and control of the weight loss. Timing signals for the logic and control functions of the generator are provided by a crystal oscillator 16. A magnetically-actuated reed switch 14 may be incorporated in the electronics package to provide the generator with manual activation capability (by use of an external magnet, not shown, placed immediately adjacent to the package or its implant site).

medical treatment of a disorder. To that end, a power down circuit (identified as 18 in a similar stimulator in FIG. 1 of U.S. Pat. No. 5,304,206 to Baker et al., the disclosure of which is hereby incorporated herein by reference in its entirety) may be electrically connected to reed switch 14 and logic/control circuit 15 and timed by the clock pulses from the crystal oscillator 16 to reduce power to the microprocessor of section 15 and/or to the oscillator to a point at which the device is essentially in a sleep state but sufficiently alert to be awakened on command. The power down mode or sleep state may be initiated automatically within a timed interval after the device has been activated to generate its programmed stimulating output signal. Alternatively, the device may stay in a reduced power state until the microprocessor is awakened by manual activation of the device by the patient.

Referring to instant FIG. 1 herein, built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by trained, certified, personnel) by means of the external computer and the programming wand.

Logic and control section 15 of the stimulus generator 10 controls an output circuit or section 19, which generates the programmed signal levels appropriate to the disorder being treated. The output section and its programmed output signal are coupled (directly, capacitively, or inductively) to an electrical connector 20 on the housing 21 of the generator and to lead assembly 22 connected to the stimulating electrodes (FIGS. 2 and 3).

Housing 21 in which stimulus generator 10 is encased is hermetically sealed and composed of a material such as titanium, which is biologically compatible with the fluids and neurostimulator are available in the '985 application.

FIG. 2 illustrates one location where the generator 10 may be implanted, in case 21 with connector 20, in the patient's chest in a cavity formed by the implanting surgeon just below the skin, much as a pacemaker pulse generator would be implanted. As discussed elsewhere, the location of the generator may vary with each patient and may be placed in on a patient's arm, under the skin in the neck area either proximal or distal to the site where the stimulating electrodes are attached to the vagus nerve. For some patients, wireless transmissions of stimulating signals replace the implantable generator. A stimulating nerve electrode set 25 (FIG. 3) is conductively connected to the distal end of insulated electrically conductive lead assembly 22, which is attached at its proximal end to connector 20. Electrode set 25 is a bipolar stimulating electrode, preferably of the type described in U.S. Pat. No. 4,573,481 issued Mar. 4, 1986 to Bullara, the teachings of which are herein incorporated by reference in their entirety. The electrode assembly is surgically implanted on the vagus nerve 27 in the patient's neck. The two electrodes 25-1 and 25-2 are wrapped about the vagus nerve, and the assembly is secured to the nerve by a spiral anchoring tether 28 desirably as disclosed in U.S. Pat. No. 4,979,511 issued Dec. 25, 1990 to Reese S. Terry. Jr., the teachings of which are herein incorporated by reference in their entirety. Lead(s) 22 is secured, while retaining the ability to flex with movement of the chest and neck, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve).

Eye movement sensing electrodes 33 may be implanted at or near the outer periphery of each eye socket in a suitable location to sense muscle movement or actual eye movement, as shown in FIG. 2, and electrically connected to leads 34 implanted via a catheter or other suitable means (not shown) and extending along the jawline through the neck and chest tissue to the sense signal analysis circuit 23 of stimulus generator 10. Alternatively, or additionally, EEG sense electrodes 36 may be implanted in spaced apart relation through the skull, and connected to leads 37 implanted and extending along the scalp and temple and then along the same path and in the same manner as described above for the eye movement electrode leads. These or other types of sensing electrodes would only be required for alternative embodiments of the invention, since the preferred embodiment utilizes a continuous, periodic or intermittent stimulus signal applied to the vagus nerve (each of which constitutes a form of continual application of the signal).

The stimulus generator may be programmed with an IBM/Unix/Linux-compatible personal computer (not shown) using suitable software based on the description herein, and a programming wand (not shown). The wand and software permit noninvasive communication with the generator after the latter is implanted. The wand is preferably powered by internal batteries, and provided with a "power on" light to indicate sufficient power for is occurring between the wand and the generator.

The device parameters may be varied to provide the optimal nerve stimulation for each individual patient. In one embodiment, patients typically received 0.75 mA and pulse width of either 250 microsecond (µs) or 500 microsecond (µs) (Example 1). The method of the invention comprises providing chronic pre-programmed vagal stimulation to a patient in the neck either unilaterally or bilaterally. Desirably, the patient is treated for a six to twelve month period or longer. The amount of weight loss obtained using the method of the invention will vary between patients, with the heaviest patients showing the greatest weight loss. There is no known limit to the period of treatment that can be safely and effectively applied to an obese patient, while those with normal weight will maintain their weight if treated according to the present invention methods.

The present inventors appear to be the first to recognize that the above treatment method, which is similar to methods used to treat epilepsy for several years, provides a method to lose weight without invading the abdomen or thorax. The invention shows that rather than a side-effect [which Burneo et al., supra, considered unpredictable and hence necessary to include in warnings to patients and physicians considering VNS for treatment of epilepsy], cervical VNS induces weight loss reliably based upon the initial weight of the person. The method shows that proper selection of patients (i.e., BMI>30) and timing (6 months-one year) are critical for weight loss. The device used for VNS, unlike current devices, need not have any sensing capabilities; therefore, cost reductions are possible. Placement in the neck should allow simple attachment to the vagus nerve and should require only local anesthesia and surgical outpatient, same-day procedures. The invention is [in part] a method to induce weight loss and maintain normal weight in the obese without changing lifestyle or diet.

pulse generator system similar to that described in U.S. Pat. No. 6,449,512 ("the '512 patent", the disclosure of which is hereby incorporated herein by reference in its entirety) to Boveia, for treatment of urological disorders. The implantable pulse generator for use in the present invention comprises prepackaged/predetermined programs stored in the memory of the pulse generator, and means for accessing these with an external control element, such as a magnet. For instance, U.S. Pat. No. 5,722,998 to Prutchi et al. (the disclosure of which is hereby incorporated herein by reference in its entirety) discloses an implantable medical device that includes a giant magnetoresistance ratio (GMR) sensor to detect the presence of a magnet in order to command the device to enter a predetermined mode of operation. Alternatively, U.S. Pat. No. 5,304,206 to Baker, Jr. et al. (the disclosure of which is hereby incorporated herein by reference in its entirety) discloses activation techniques for an implantable medical device, including an activation means which is responsive to a patient-initiated signal to activate, or in some instances to deactivate, the stimulus generator. According to one aspect of the invention, the neurostimulator is adapted to be activated to the "on" state in response to tapping by the patient on the skin overlying the implant site. Alternative manual activation is also enhanced by incorporating a pushbutton which is readily depressed for electrical actuation of the implanted device, using a miniaturized generator in the bracelet to transmit an audio or supersonic signal for detection by circuitry within the implanted neurostimulator.

In any case, the programmerless implantable pulse generator is adapted to selectively activate predetermined programs with the external control system, thereby eliminating the need for an external programming device, resulting in significant cost reduction with essentially the same functionality as an externally programmable stimulus generator. For instance, the '512 patent" to Boveja, for treatment of urological disorders, teaches a device in which the number of predetermined programs can be 100, but for patient convenience, less predetermined programs, arranged in such a way that the aggressiveness of the therapy increases from program #1 to Program #9.

In one aspect, therefore, the present invention, provides an apparatus for neuromodulation of a vagus nerve, comprising: a) an implantable lead having at least one electrode adapted to be in contact with a cervical vagus nerve and connected to a programmerless pulse generator which comprises circuitry, a power source, and at least two predetermined programs to control electrical signals; b) means to control the at least two predetermined programs by an external control system, whereby the implantable pulse generator provides neuromodulation therapy which is controllable by an external control system. The external control system is selected from the group consisting of a magnetically activated control system, a mechanically sensitive activation system that is adapted to be activated to the "on" state in response to tapping by the patient on the skin overlying the implant site, and an activation system responsive to an audio or supersonic signal generated by an external control device. The electrical signals controlled by the apparatus comprise at least one variable component selected from the group consisting of the current amplitude, pulse width, frequency, on-time and off-time, and the at least two predetermined programs control the variable component of those electrical signals. Device parameters controlled by the programs include: the output current which is ramped up gradually (e.g., in 0.23 mA increments) to one of several final values between about 0.5 to about 1.5 mA (typically, 0.75 mA) depending on patient tolerance; stimulation frequency, typically 20 or 30 Hz but optionally another value in the range of 10-100 Hz; pulse width in the range of 100 to 1000 microseconds ($\mu$s), typically either 250 $\mu$s or 500 $\mu$s; and device (duty) cycle on for a substantially shorter time than off, for instance 10 to 100 s on out of each 3 to 10 minute period, preferably 30 s on in every five minutes of signal application. For patient comfort is ramped up and ramped down, instead of providing abrupt delivery and cessation of electrical pulses.

In another aspect the invention provides a method wherein the vagus nerve signal stimulus is applied at a portion of the nervous system remote from the vagus nerve such as at or near the esophageal wall, for indirect stimulation of the vagus nerve in the vicinity of the cervical location. Here, at least one signal generator is implanted together with one or more electrodes subsequently operatively coupled to the generator via lead(s) for generating and applying the electrical signal internally to a portion of the patient's nervous system other than the vagus nerve, to provide indirect stimulation of the vagus nerve in the vicinity of the desired location. Alternatively, the electrical signal stimulus may be applied non-invasively to a portion of the patient's nervous system other than the vagus nerve per se, for indirect stimulation of the vagus nerve at a cervical location. For instance, U.S. patent application Ser. No. 2002/0183237 by Puskas, published Dec. 5, 2002 (the entire disclosure of which is hereby incorporated herein by reference), discloses methods for indirectly stimulating a vagus nerve of a patient which includes the steps of positioning one or more electrodes in the vicinity of the vagus nerve and then actuating the electrode(s) to create an electrical field for stimulating the vagus nerve. Disclosed embodiments include positioning one or more electrodes in the esophagus, trachea, or jugular vein, on the neck of the patient, and combinations thereof.

Functional brain imaging (PET) scans performed on patients receiving chronic vagus nerve stimulation and exhibiting weight loss show that various regions of the brain are involved. The brain regions that were affected included the midbrain (Substantia Nigra or SN/Ventral tegmental area or VTA) and the ventromedial prefrontal cortex (VMPFC).

Example. It will be apparent to those skilled in the art that many changes can be made in the embodiments described in the Examples without departing from the scope of the present invention. Thus, the scope of the present invention should not be limited to the embodiments described in this application, but only by the embodiments described by the language of the claims and the equivalents of those embodiments.

EXAMPLE 1

Fourteen patients were treated with chronic vagus nerve stimulation. Four men and ten women, with an average age of 46 years (SD±10) were treated. All but two (Hispanic and Middle Eastern) were Euro-Americans. The mean weight on intake was 91 kg (SD±27, range 46 to 137 kg) with a body mass index (BMI) of 43 kg/m$^2$ (SD±5, range 18 to 49 kg/mn$^2$). The average weight loss at one year was 7 kg (SD±3, range −6 to +24) with a mean drop in BMI at one year of 2 kg/m$^2$ (SD±3, range −2 to +8)k. All patients denied making any major attempts to diet or exercise during the study. Medication changes of all patients were minimized during the study.

Figure 6:
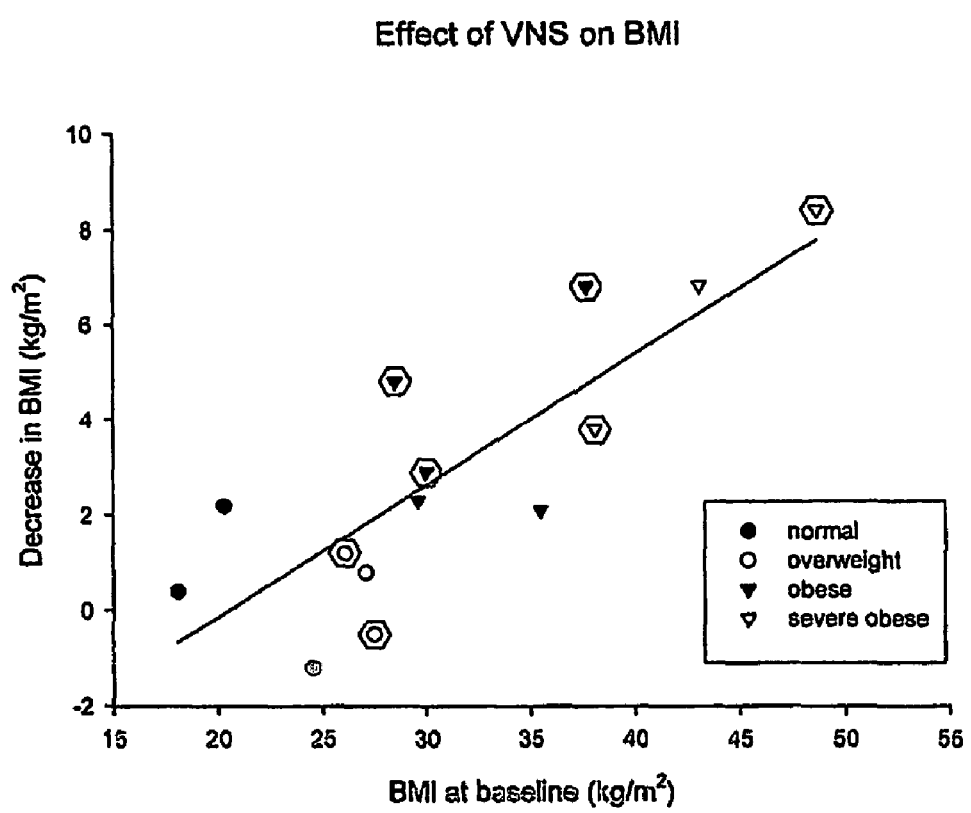
FIG. 6 shows the relationship between a patient's BMI after one year of vagus nerve stimulation and the patient's BMI at the beginning of the study. Patients whose positron emission tomographic (PET) scans were determined are highlighted with hexagons.

The neurostimulator device described above was implanted under the skin of the chest, and connected in the neck to the trunk of the left vagus nerve. Default device parameters were used except for the output current was from about 0.5 to 1.5 mA (most patients received 0.75 mA) and the pulse width was either 250 $\mu$s or 500 $\mu$s. The device cycled on for 30 s every five minutes. After chronic vagus nerve stimulation for a six to twelve month period, several patients characterized as obese at the beginning of the treatment had marked weight loss, while those with normal weight maintained their weight. The heaviest patient initially weighed 137 kg (BMI 49 kg/m$^2$) and after one year of vagus nerve stimulation in accordance with the method of the invention the patient weighed 114 kg (BMI 40 kg/m$^2$), a decrease of 24 kg. FIG. 6 shows that the decrease in BMI of individual patients was consistently equivalently, the loss of weight was proportional to the initial weight. This linear relationship accounted for two-thirds of the variance (r$^2$=64%).

Figure 7:
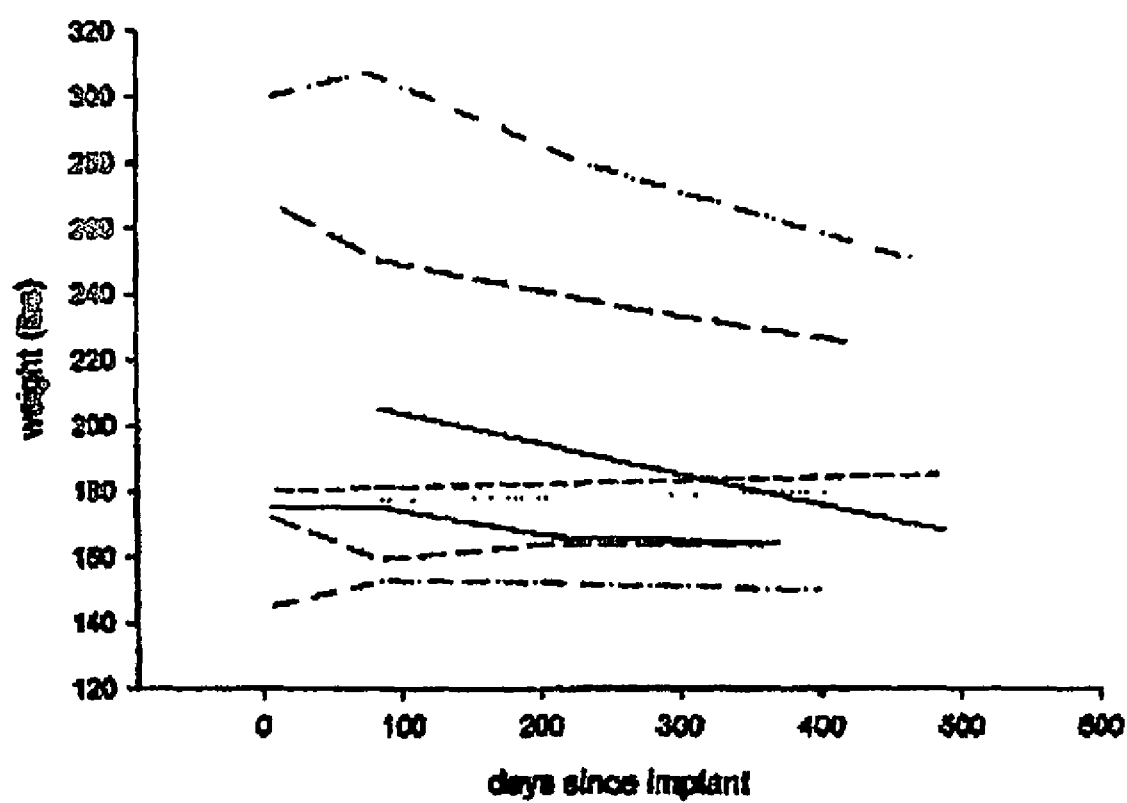
FIG. 7 shows weights taken for each patient as a function of time after initiation of the VNS study, up to 500 days.

FIG. 7 shows weights taken for each patient as a function of time after initiation of the VNS study, up to 500 days. Each line represents a single patient. Straight lines connect pairs of points for an individual; missing data were interpolated. This plot shows the change in weight (or, because height does not change in this time scale, BMI) as a function of the number of days since implantation of the device (for patients in the treatment arm, the VNS device was turned ON about two weeks after implanting; for those in the control arm, the device was turned ON at the end of the trial (i.e., 120 days).

The figure demonstrates several points: (1) There is no significant change in weight overall during the first interval of 120 days. In PET scans taken at this time, the final (at one year) pattern of deactivation from the PET scans was not visualized. (2) The first indication for weight loss at 180 days coincides with the earliest changes in brain metabolic activity at regions templated to the final results. (3) For those over 200 lbs initially, there is a clear and consistent decrease in weight. Given the variance in the data for those under 200 lbs, it is difficult to support statistical models not indicating a causal relationship, such as a hypothesis that the three heaviest patients are outliers or represent some sort of phenomenon such as regression to the mean (where obese patients would decrease in weight while those whose weights were less would increase in weight). (4) In some cases there is data extending beyond 400 days, suggestive of further decreases in weight in the morbidly obese, whereas those under 200 lbs do not show further weight loss.

The patients in this study were enrolled in a trial testing the efficacy of cVNS for severe clinical depression unresponsive to conventional treatments. The change in weight during cVNS was not significantly related to changes in the level of depression during respond to the depression treatment. In fact, the most obese patient, who lost the most weight, was more depressed after the trial (Hamilton depression score went from 37 to 49). No patient intentionally altered activity or implemented diets. Anecdotally, the obese patients felt that their appetite had normalized during treatment. Of note, weight loss as a potential outcome of cVNS therapy was unknown at the time of the trial and was not listed in the informed consent. No patient reported spontaneously weight loss; none considered that the weight loss was related to cVNS therapy. cVNS therapy was tolerated well; only one patient requested removal of the device because of lack of efficacy for her depression.

Thus, among the patients in this study, this data provides evidence that chronic vagus nerve stimulation applied to the nerve in the patient's neck affected a consistent and reliable reduction of weight. Weight loss occurred gradually over one year and some of the most obese patients continued to lose weight thereafter. The amount of weight loss was proportional to the initial severity of the obesity.

For Positron Emission Tomography (PET), patients fasted at least eight hours. Two hours before scanning, the cVNS device was turned off with the magnet to avoid imaging the direct effects of electrical stimulation. An ECAT EXACT camera (Siemens, Knoxville, Tenn.) was operated in 2-D mode with septae extended. The instrument's field of view was 15 cm, covering the whole brain. A transmission scan was collected for attenuation correction. Patients received $^{18}$F-fluorodeoxyglucose (5 mCi/70 kg up to 10 mCi maximum) intravenously and rested quietly during uptake with eyes closed and ears unplugged in a quiet, darkened room. A static emission scan was obtained containing approximately ~15 million counts. Data were corrected for electronic deadtime and randoms. A previous quantitative study with arterial catheters of the cerebral metabolic rate for glucose in subjects with normal weight versus patients with severe obesity (but without diabetes) did not find whole-brain or Cognitive Neurology, London, GB). Global whole-brain normalization was adjusted proportionately. A linear, random effects model was selected to test the contrast (post-cVNS[one year] minus pre-cVNS). Coordinates of activation foci (x,y,z) in mm are referenced to the bicommissural planes (atlas of Talairach and Tournoux, 198816). Magnitudes of activation are reported in terms of Z-scores (mean/SD).

Identification of changes in regional brain activity induced by chronic cVNS may help clarify mechanisms and suggest new therapeutic pathways to weight reduction. Here, we report the neuroimaging results from the seven subjects (denoted by hexagons in FIG. 6) who were overweight (BMI>26 kg/m2) and who gave written informed consent for PET scanning. Not all of these patients provided data at three months and six months, while all seven provided data at one year. The interval data will not be presented, but at six months, the PET data appeared consistent with, but less robust, than that at one year.

Table 1 shows the negative and positive changes in brain metabolism identified in the difference image: [post-cVNS (one year) minus pre-cVNS] with a conservative threshold Z-scoreore=4.5. Although we report local maxima and minima, the pattern of change in medial prefrontal cortical metabolism appeared broad, rather than clearly-resolvable, separate activation foci; perhaps consistent with widespread neuromodulation across brain regions. Brain metabolism was reduced after treatment in several structures: medial prefrontal cortex (Brodmann area, BA, 9 with extension into polar and ventromedial prefrontal cortex (VMPFC); ventral tegmentum (VTA)/substantia nigra (SN) at [x,y,z]=[12,−20,−8]; and hypothalamus at [x,y,z]=[0,−14,−2]; see FIG. 2. Brain metabolism was increased after cVNS treatment in the inferior cerebellum, inferior parietal cortex (BA 40) and fusiform gyrus (BA 37).
cVNS (one year) minus pre-cVNS].

| | | | Post-cVNS minus Pre-cVNS | | | |
|---|---|---|---|---|---|---|
| | | | | Coordinates | | |
| Region | BA | Side | x | y | z | Z-value |
| Decreases in metabolism | | | | | | |
| Medial Frontal Gyrus | 9 | Left | −6 | 54 | 30 | −5.4 |
| Middle Frontal Gyrus | 6 | Right | 40 | 14 | 52 | −4.6 |
| VTA/SN | | Right | 12 | −20 | −8 | −4.5 |
| Hypothalamus | | Midline | 0 | −16 | −2 | −4.5 |
| Increases in metabolism | | | | | | |
| Inferior Cerebellum | | Left | −16 | −56 | −50 | 5.3 |
| Fusiform Gyrus | 37 | Right | 38 | −46 | −16 | 4.8 |
| Inf. Parietal Lobe | 40 | Left | −44 | −28 | 24 | 4.7 |

The major target of the vagus nerve is the nucleus of the solitary tract. This nucleus was not visualized here, probably because of its small size with respect to the resolution of PET. The vagus indirectly innervates many brainstem nuclei including those in the VTA/SN and hypothalamus. The SN (A9) has dopamine neurons innervating the neostriatum, while the VTA (A10) has dopamine neurons innervating prefrontal and paralimbic cortices (VMPFC, cingulate, and entorhinal regions) and associated structures (nucleus accumbens, amygdala, etc.). PET can not resolve VTA from SN, but based on the observed pattern of changes in brain activity, VTA is the more likely target of cVNS.

We cannot dissect unambiguously which components of the involved neural network might relate to weight loss versus mood disorder. The network is not typical of drug treatment of depression; however, such studies do not focus on severe, chronic, treatment-resistant depression. These two phenomena (i.e., weight loss and antidepressant action) appear independent since there was no significant correlation between depression scores and BMI. The central role of the hypothalamus in weight control adds support to this network's cVNS studies of obese patients without depression will be necessary to definitively isolate the effects of weight alone.

In conclusion, chronic cVNS offers potential as a new treatment for severe obesity. Patients with near-normal BMI get little weight loss; morbidly obese patients show the greatest weight loss. The brain correlates of treatment with chronic cVNS in these patients is a network of deactivated structures including VTA/SN, hypothalamus, and VMPFC. Much of this network overlaps with the circuitry of reward processing and dopamine neurotransmission. These results identify an urgent need for a full-fledged, controlled, clinical trial of cVNS for the treatment of severe obesity alone. Despite some invasiveness, cVNS appears justifiable in such a trial given potential benefits versus the known morbidity and mortality of persistent severe obesity in children, adolescents, and adults.

The present invention may be embodied in other specific forms without departing from the essential attributes thereof. Therefore, the illustrated embodiments should be considered in all respects as illustrative and not restrictive, reference being made to the appended claims rather than to the foregoing description to indicate the scope of the invention.

The invention claimed is:

1. A method of treating morbid obesity in a patient, said method comprising:
   implanting subcutaneously in a morbidly obese patient
      a device comprising an electrical signal generator and a predetermined program for controlling at least one parameter of the electrical signal, and
      at least one electrical lead having at least one proximal electrical connector and one distal nerve electrode;
   operably connecting a proximal electrical connector of the electrical lead to the signal generator;
   operably coupling a distal nerve electrode of the electrical lead to the trunk of only the left vagus nerve in the neck of the patient, and
   activating the signal generator to chronically stimulate the vagus nerve with an electrical signal for a period of at least six months in accordance with the program;
   whereby the method induces weight loss and maintains normal weight in the patient without changing lifestyle or diet.

2. The method of claim 1, wherein:
   said electrical signal comprises at least one variable parameter selected from the group consisting of current amplitude, pulse width, pulse frequency, and a duty cycle of alternating intervals with power on and power off,
   said device comprises at least two predetermined programs for controlling at least one parameter of said electrical signal according to a programmed regimen that cannot be altered while said device is implanted in the patient;
   said signal generator is activated by an externally activated control system that selectively activates each of said at least two predetermined programs; and
   said apparatus provides vagus nerve stimulation which is controllable by said externally activated control system.

3. The method of claim 2, wherein said externally activated control system is selected from the group consisting of a magnetically activated control system, a mechanically activated control system that responds to tapping on the skin near said device, and an acoustically activated control system that responds to an audio or supersonic signal.

4. The method of claim 2, wherein each of said at least two predetermined programs to control parameters of said electrical signal produces an electrical signal that has an output current amplitude between about 0.5 mA to about 1.5 mA, a stimulation frequency between about 10 Hz and 100 Hz, a pulse width in the range of 100 microseconds to 1000 microseconds (μs), and a duty cycle of intervals with power on for about 10 s to about 100 s and power off for the remainder of a 3 minute to 10 minute period of treatment.

5. The method of claim 2, wherein at least one of said at least two predetermined programs to control parameters of said electrical signal produces an electrical signal that comprises an output current amplitude of about 0.7 mA, a stimulation frequency of about 30 Hz, a pulse width of either about 250 microseconds or about 500 microseconds (μs), and a duty cycle of intervals with power on for about 30 s and power off for the remainder of a 5 minute period of treatment.

6. Apparatus for treating morbid obesity in a patient, said apparatus comprising:
   a device suitable for implanting subcutaneously in a morbidly obese patient and at least one implantable electrical lead,
   said device comprising an electrical signal generator,
   said electrical lead having at least one proximal connector for operably connecting said electrical lead to said signal generator and at least one distal nerve electrode for operably coupling said electrical lead only to left trunk of the vagus nerve in the neck of the patient;
   said signal generator comprising a power source suitable to chronically stimulate said trunk of the vagus nerve with an electrical signal while implanted for a period of at least one year,
   said electrical signal having at least one variable parameter selected from the group consisting of current amplitude, pulse width, pulse frequency, and a duty cycle of alternating intervals with power on and power off,
   said device further comprising at least two predetermined programs to reduce weight in a morbidly obese patient wherein at least one parameter of said electrical signal is controlled according to a programmed regimen that cannot be altered while said device is implanted in the patient;
   said signal generator being activated by an externally activated control system that selectively activates each of said at least two predetermined programs;
   whereby said apparatus provides chronic cervical vagus nerve stimulation which is controllable by said externally activated control system.

7. The apparatus of claim 6, wherein said external control system is selected for the group consisting of a magnetically activated control system, a mechanically activated control system that is adapted to be activated in response to tapping on the skin near said device, and an activation system responsive to an audio or supersonic signal generated by an external control component.

8. The apparatus of claim 6, wherein each of said at least two predetermined programs to control parameters of said electrical signal produces an electrical signal that has an output current amplitude between 0.5 mA to about 1.5 mA, a stimulation frequency between about 10 Hz and 100 Hz, a pulse width in the range of 100 microseconds to 1000 microseconds (μs), and a duty cycle of intervals with power on for about 10 s to about 100 s and power off for the remainder of each 3 minute to 10 minute period of treatment.

9. The apparatus of claim 6, wherein at least one of said at least two predetermined programs to control parameters of said electrical signal produces an electrical signal that has an output current amplitude of about 0.75 mA, a stimulation frequency of about 30 Hz, a pulse width of either about 250 microseconds or about 500 microseconds (μs), and a duty cycle of intervals with power on for about 30 s and power off for the remained of each 5 minute period of treatment.

* * * * *